United States Patent
Lee et al.

(10) Patent No.: US 7,942,957 B2
(45) Date of Patent: May 17, 2011

(54) AIR FILTER HAVING ANTIMICROBIAL PROPERTY

(75) Inventors: Jun Seok Lee, Kyonggi-do (KR);
Sunghak Hwang, Kyungki-di (KR);
Seongju Kim, Seoul (KR)

(73) Assignee: 3M Innovative Properties Company, St. Paul, MN (US)

(*) Notice: Subject to any disclaimer, the term of this patent is extended or adjusted under 35 U.S.C. 154(b) by 469 days.

(21) Appl. No.: 12/097,060

(22) PCT Filed: Jan. 24, 2007

(86) PCT No.: PCT/US2007/001817
§ 371 (c)(1),
(2), (4) Date: Jun. 12, 2008

(87) PCT Pub. No.: WO2007/087326
PCT Pub. Date: Aug. 2, 2007

(65) Prior Publication Data
US 2008/0317802 A1    Dec. 25, 2008

(30) Foreign Application Priority Data
Jan. 25, 2006 (KR) .................. 10-2006-0007791

(51) Int. Cl.
*B01D 46/00* (2006.01)
*A62B 7/08* (2006.01)
*A01N 25/00* (2006.01)
*A01N 25/08* (2006.01)
*A01N 59/00* (2006.01)
*B05D 1/18* (2006.01)
*B32B 5/02* (2006.01)

(52) U.S. Cl. ......... 96/226; 422/120; 424/1.29; 424/405; 424/409; 424/600; 427/430.1; 442/123

(58) Field of Classification Search ............... 96/226; 422/1, 4, 28, 37, 120; 424/1.29, 405, 408, 424/409, 600, 618; 427/430.1; 428/357; 442/59, 122; 514/188, 365, 372
See application file for complete search history.

(56) References Cited

U.S. PATENT DOCUMENTS

| | | | |
|---|---|---|---|
| 5,472,483 A * | 12/1995 | Kimura et al. | 106/18.34 |
| 5,505,770 A * | 4/1996 | Kimura et al. | 106/18.31 |
| 5,741,483 A | 4/1998 | Okawa | |
| 6,280,657 B1 * | 8/2001 | McEntee | 252/400.31 |
| 6,726,937 B2 | 4/2004 | Imai | |
| 6,846,777 B2 | 1/2005 | Antoni-Zimmermann et al. | |
| 7,429,392 B2 * | 9/2008 | Baum et al. | 424/405 |
| 7,772,156 B2 * | 8/2010 | Bryant | 504/118 |
| 2004/0234603 A1 * | 11/2004 | Baum et al. | 424/486 |
| 2007/0010598 A1 * | 1/2007 | Hamel | 523/122 |
| 2007/0053866 A1 * | 3/2007 | Abou-Nemeh | 424/78.09 |
| 2008/0102094 A1 * | 5/2008 | Bryant | 424/409 |
| 2008/0118640 A1 * | 5/2008 | Kalkanoglu et al. | 427/186 |
| 2009/0093505 A1 * | 4/2009 | Bylemans et al. | 514/275 |

* cited by examiner

*Primary Examiner* — Duane Smith
*Assistant Examiner* — Sonji Turner

(57) ABSTRACT

The present invention relates to an antimicrobial composition having antibacterial and antifungal properties and to an air filter manufactured using the composition. The filter of the present invention, comprising a filtration media treated with the antimicrobial composition having antibacterial and antifungal properties, has excellent antibacterial and antifungal properties, and thus can prevent the bacteria and fungi filtered by the filter from propagating in the filter.

12 Claims, 2 Drawing Sheets

US 7,942,957 B2

AIR FILTER HAVING ANTIMICROBIAL PROPERTY

CROSS REFERENCE TO RELATED APPLICATIONS

This application is a national stage filing under 35 U.S.C. 371 of PCT/US2007/001817, filed Jan. 24, 2007, which claims priority to Korean Application No. 10-2006-0007791, filed Jan. 25, 2006, the disclosure of which is incorporated by reference in its/their entirety herein.

TECHNICAL FIELD

The present invention relates to an antimicrobial composition for air filters, having antibacterial and antifungal properties, and a filter manufactured using a filtration media treated with said antimicrobial composition. The filter according to the present invention has a function of collecting fine dust and also excellent antibacterial and antifungal properties, and thus can filter most microorganisms in air, including bacteria and fungi, and can inhibit growth of these microorganisms on the surface thereof, even when it is used for a long period of time.

BACKGROUND ART

These days, as air pollution becomes severe, many hazardous substances and pollutant dust, which are harmful to the human body, are contained in air. When air containing such hazardous substances and pollutant dust, harmful to the human body, is ingested without any filtration, it will have various adverse effects on the human body. For this reason, air cleaners having various types of filter systems for filtering the hazardous substances and pollutant dust are used.

The filter system of the air cleaners according to the prior art generally comprise a pretreatment filter, a medium filter, a deodorizing filter, a HEPA (High Efficiency Particulate Air) filter and a blower fan. Generally, microorganisms harmful to the human body have a size of a few microns, and such microorganisms are removed through the HEPA filter in the filter system.

This HEPA filter is a kind of filtration media and can be made of, for example, polypropylene fiber, which is a special charged fiber. The HEPA filter is mounted in the air cleaner to filter even fine hazardous substances and pollutant dust. Also, the HEPA filter has a strong adsorption capability to completely remove house hazardous substances such as dust, mites, viruses and fungi, which are contained in air and are harmful to the human body, and pollutant particulate matter having a size of about 0.3 microns, which is very harmful to the human body, at a high removal rate of 99.9%. Thus, it serves to purify polluted air to a significantly clean state.

FIG. 1 shows a HEPA filter according to the prior art. As shown in FIG. 1, the prior filter system has a structure in which a filtering media including the HEPA filter is mounted in a case 110 formed of a plastic material.

Although prior microporous filters such as HEPA filters have excellent performance in removing microorganisms suspended in air, including general bacteria, microorganisms, which are not removed or filtered through the prior filters, still exist. Meanwhile, in the case of such types of filters, microorganisms filtered through a filter media sometimes remain on the surface of the filtration media. As a result, these microorganisms continue to grow without being discharged with purified air, so that these microorganisms cause odors when the filter is used for a long period of time. Thus, these microorganisms act as the cause of secondary contamination, which reduces the air purification performance of the filter.

In an attempt to solve the above problem, there is a method in which a separate antibacterial filter is placed in the front or rear of the HEPA filter. However, this method has problems in that an increase in the number of filter media causes pressure loss and leads to an increase in production cost. In another attempt, there is a method in which the surface of the HEPA filter is coated with antibacterial substances, but this method has a disadvantage in that the dust collection efficiency of the filter is reduced.

DISCLOSURE OF THE INVENTION

Accordingly, the present inventors have conducted studies in order to solve the above-mentioned problems occurring in the prior art and to prepare an antimicrobial agent for air filters, which can filter or remove almost all microorganisms in air. Also, the present inventors have conducted studies on a method which can maximize the activity of said antimicrobial agent while maintaining the activity of the antimicrobial agent for a long period of time, when the antibacterial agent is applied to air filters.

As a result, the present inventors have developed a composition having a broad antimicrobial spectrum, which exhibits growth inhibitory activity against various microorganisms, including bacteria and fungi, by mixing antimicrobial components, including isothiazoline derivatives, thiabendazole, nanosilver or zinc pyrithione, with a stabilizer consisting of a silicone copolymer, and a binder consisting of acrylic resin, urethane resin or silicone resin. Also, the present inventors have found that, when the backing media or cover web of the filtration media is treated with said antimicrobial composition, the antimicrobial activity of the filter can be increased.

Accordingly, it is an object of the present invention to provide an antimicrobial composition having a broad antimicrobial spectrum, as well as a preparation method thereof.

Another object of the present invention is to provide a filter treated with said antimicrobial composition. Stilt another object of the present invention is to provide a method for manufacturing said filter.

To achieve the above objects, according to one aspect of the present invention, there is provided an antimicrobial composition comprising: 4,5-dichloro-2-n-octyl-4-isothiazolin-3-one and 2-n-octyl-4-isothiazolin-3-one as antimicrobial active ingredients; a stabilizer consisting of at least one silicone compound selected from among volatile silicone oil and silicone resin; a binder selected from among acrylic, urethane resin and silicone resin; and water. According to one embodiment of the present invention, the antimicrobial composition can be provided in the form of a water-dispersible composition in which the components thereof are dispersed in water.

The composition can comprise antimicrobial active ingredients, including thiabendazole, nanosilver and zinc pyrithione, if necessary.

As used herein, the term "antimicrobial" is intended to cover both antibacterial and antifungal.

According to another aspect of the present invention, there is provided a method for manufacturing a filtration media, which includes a cover web, a filtering part and a backing media, the method comprising the steps of: diluting said antimicrobial composition in water to prepare a dilution of the antimicrobial composition; treating the backing media or cover web of the filter media with the dilution and drying the treated backing media or cover web; and arranging the dried backing media or cover web together with other members of the filtration media. The step of treating the backing media or cover web of the filtration media with the dilution can be conducted by dipping the backing media or cover web of the filtration media in the dilution or spraying the dilution onto the backing media or cover web of the filtration media.

According to still another aspect, there is provided an air filter comprising: a filtration media prepared according to said method; and a filter frame for settling the filtration media.

BRIEF DESCRIPTION OF THE DRAWINGS

The foregoing and other objects, features and advantages of the present invention will become more apparent from the following detailed description when taken in conjunction with the accompanying drawings in which.

BEST MODE FOR CARRYING OUT THE INVENTION

Figure 1:
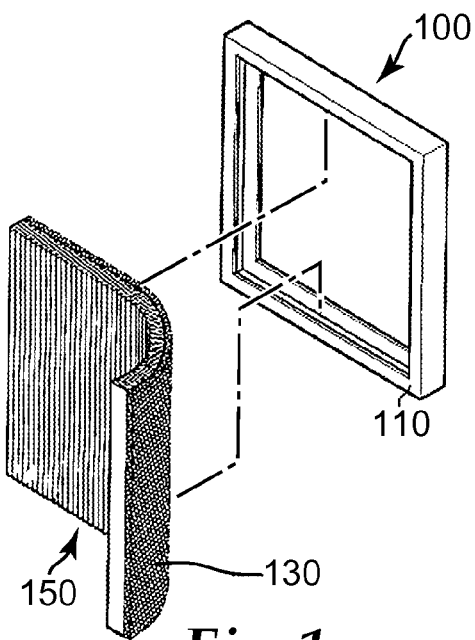
FIG. 1 is a perspective view showing one example of a HEPA (High Efficiency Particulate Air) filter according to the prior art.

Reference will now be made in detail to the preferred embodiments of the present invention.

An antimicrobial composition according to the present invention can be prepared in the form of a water-dispersible composition, the active ingredients of which are dispersed in water.

Among the active ingredients, active ingredients having antimicrobial activity include 4,5-dichloro-2-n-octyl-4-isothiazolin-3-one and 2-n-octyl-4-isothiazolin-3-one, which have antibacterial and antifungal activities. If necessary, antibacterial/antifungal active ingredients, including thiabendazole, nanosilver and zinc pyrithione, can be added to enlarge the antimicrobial spectrum of the composition and to reduce the water solubility of the composition, resulting in an increase in durability.

As said 4,5-dichloro-2-n-octyl-4-isothiazolin-3-one and 2-n-octyl-4-isothiazolin-3-one, commercially available products can be used.

Among other components, 2-n-octyl-4-isothiazolin-3-one is present in a liquid state, and thus has high initial antibacterial activity and an excellent adsorption capability. Thus, when it is applied to filters, it can function to increase initial antibacterial and antifungal effects. Also, 4,5-dichloro-2-n-octyl-4-isothiazolin-3-one is present as a solid phase upon mixing with a binder resin, and thus, when it is in contact with air, it will be slowly released to show long-lasting antibacterial and antifungal effects.

Said 4,5-dichloro-2-n-octyl-4-isothiazolin-3-one can be contained in the composition in an amount of 1-10 wt % based on the total weight of the composition. If the content of 4,5-dichloro-2-n-octyl-4-isothiazolin-3-one is less than 1 wt %, it will be difficult to show sufficient antibacterial and antifungal effects, and if the content is more than 10 wt %, it can adversely affect the human body due to excessive antibacterial and antifungal properties.

Said 2-n-octyl-4-isothiazolin-3-one can be contained in the composition in an amount of 1-15 wt % based on the total weight of the composition. If the content of 2-n-octyl-4-isothiazolin-3-one is less than 1 wt %, it will be difficult to show sufficient antibacterial and antifungal effects, and if the content is more than 15 wt %, it can adversely affect the human body due to excessive antibacterial and antifungal properties.

Also, thiabendazole, nanosilver and/or zinc pyrithione can be contained in the composition in an amount of 0.5-10 wt % based on the total weight of the composition. Thiabendazole and zinc pyrithione have the effect of increasing antifungal activity, and nanosilver serves to increase antibacterial effects. These components can be used in a suitable mixture, if necessary. The addition of these components can have a synergistic effect on the antimicrobial performance of the composition. As used herein, the term "nanosilver" means nano-sized silver particles, including nano-sized silver or silver oxide.

A stabilizer is used to stabilize the antimicrobial active ingredients in the composition. In the present invention, silicone compounds can be used as the stabilizer. According to one embodiment of the present invention, volatile silicone oil and silicone resin can be used. These silicone compounds can be used alone or in a mixture. The silicone compounds can promote the dispersion of the antimicrobial active ingredients and the binder in water to stabilize the antimicrobial active ingredients and to make the active ingredients aqueous, thereby making it possible to prepare a water-dispersible composition. Also, when the water-dispersible antimicrobial composition is diluted with water before use, the silicone compounds serve to prevent the formation of precipitates or solids. This stabilizer can be contained in the composition in an amount of 1-10 wt % based on the total weight of the composition.

As described above, in the present invention, silicone compounds, including volatile silicone oil and silicone resin, are used instead of surfactants in order to make the antimicrobial active ingredients aqueous and to stabilize the active ingredients.

Also, a binder is used to impart an adhesive property to the antimicrobial composition according to the present invention and to increase the durability and elasticity of a filtration media treated with either said antimicrobial composition or a dilution thereof. As the binder, at least one selected from among acrylic resin, urethane resin and silicone resin can be used. The binder can be used in an amount of 20-80 parts by weight based on 100 parts by weight of the antimicrobial composition.

As described above, in the antimicrobial composition according to the present invention, acrylic resin, urethane resin or silicone resin is used to increase durability, flexibility and elasticity, and silicone is used to increase water or oil repellency and contamination resistance.

The antimicrobial composition according to the present invention may further comprise an antifoaming agent.

As the antifoaming agent, organosiloxane or polyalkylene glycol derivatives can be used. This antifoaming agent can be used in an amount of 0.01-0.5 wt % based on the total weight of the composition.

In addition to the antifoaming agent, a deodorant catalyst and the like can be additionally used.

According to another aspect, the present invention provides a method for manufacturing a filtration media 1, which includes a cover web 2, a filtering part 3 and a backing media 4, the method 10 comprising the steps of: diluting said antimicrobial composition in water to prepare a dilution of the antimicrobial composition; treating the backing media or cover web of the filter media with the dilution 11 and drying the treated backing media or cover web 14; and arranging the dried backing media or cover web together with other members of the filtration media. The step of treating the backing media or cover web of the filtration media with the dilution can be conducted by dipping the backing media or cover web of the filtration media in the dilution 11 as shown in FIG. 2 or spraying the dilution onto the backing media or cover web of the filtration media.

The dilution can be prepared by diluting 100 parts by weight of the antimicrobial composition in 500-5000 parts by weight of water. In the step of preparing the dilution, an antifoaming agent can be added.

In the present invention, the backing media or cover web of the filtration media is treated with the antimicrobial composition. The antimicrobial composition can be used after being diluted as described above, and the treatment of the backing media or cover web of the filtration media with the dilution can be performed by dipping the backing media or cover web in the dilution 11 and then drying the treated backing media or cover web 12. This is schematically shown in FIG. 2. Alternatively, the treatment of the backing media or cover web of the filtration media with the dilution can be performed by spraying the dilution onto the backing media or cover web of the filtration media.

Figure 2:
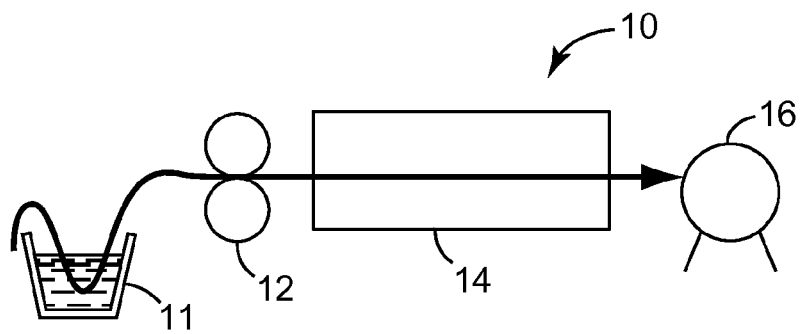
FIG. 2 is a schematic diagram showing a process of treating the backing media of a filtration media with an antibacterial and antifungal composition according to one embodiment of the present invention for manufacturing the filtration media.
Figure 3:
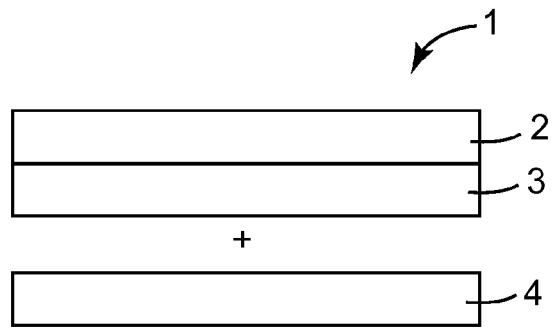
FIG. 3 is a schematic diagram showing one example of the structure of a filtration media according to the present invention, in which the filtration media includes a cover web, a filtering part and a backing media.

As shown in FIG. 2, the present invention enables the antimicrobial composition to be attached and coated onto the filtration media in an easy and convenient manner.

In comparison with the prior method in which the filtering part of the filtration media is treated with an antimicrobial composition, the method according to the present invention has advantages in that it can prevent a reduction in the filtration efficiency of the filter, and can improve the contamination resistance of the filter by treating the backing media or cover web placed in the outer portion of the filter.

The filtering part serves to substantially filter and purify air, and can be constructed by processing general purpose resin, for example, polypropylene (PP) or polyethylene (PE) into a non-woven fabric structure having micropores. Any person skilled in the art to which the present invention pertains will appreciate that it is possible to apply all non-woven fabrics used in a non-woven fabric manufacturing process, including not only staple fiber and filament fiber, but also melt blown nonwoven fabrics.

The shape of the filtering part is not specifically limited. The filtering part can be curved or flat in shape. For example, the filtering part may also have zigzag folds formed therein.

According to another aspect, the present invention provides a filtration media manufactured according to said method. Also, the present invention provides an air filter comprising said filtration media fixed by means of a filter frame. The filter frame can be made of non-woven fabric applied with polypropylene resin, elastic urethane resin or hot melt.

Hazardous substances, including house dust, mites, virus and fungi, and pollutant particulate matter having a size of about 0.3 microns, which are contained in air and harmful to the human body, can be completely removed through the antimicrobial composition having antibacterial and antifungal properties at a high removal rate of about 99.9%. Particularly, the antimicrobial composition having antibacterial and antifungal properties, which is uniformly dispersed over the filtration media, has not only the ability to remove substances harmful to the human body, but also antimicrobial activity against various microorganisms contained in air, including bacteria and fungi, and thus can purify polluted air to a significantly clean and fresh state.

The filtration media according to the present invention can be easily manufactured without complexities such as secondary processing, because the backing media or cover web thereof is treated with the antimicrobial composition. Particularly, the antimicrobial active ingredients having fine particle size, dispersed over the filtration media, can show high antimicrobial performance on the surface of the filtration media to inhibit microbial growth in the filter, thus solving a secondary pollution problem.

In other words, unlike the prior filters, the filter according to the present invention has excellent antimicrobial properties because it can exterminate microorganisms, such as bacteria or fungi, remaining in the filtration media after filtration, or inhibit the growth of the microorganisms. As a result, the inventive filter can prevent secondary contamination that causes, for example, a bad smell in purified air, which can occur when the prior filter is used for a long period of time. Also, the inventive filter can prevent the cause of the secondary contamination. In addition, the present invention eliminates a need to place a separate antibacterial filter in the front or rear of the filter, and thus significantly reduces unnecessary processes or cost caused by the secondary processing.

Hereinafter, the present invention will be described in further detail with reference to examples. It is to be understood, however, that these examples are for illustrative purposes, and the scope of the present invention is not limited thereto.

EXAMPLES 1-3

1. Preparation of Antimicrobial Compositions

Antimicrobial compositions shown in Table 1 below were prepared. The prepared antimicrobial compositions were designated as Examples 1, 2 and 3, respectively, and were used to prepare dilutions thereof, and filtration media and filters, treated with the dilutions.

TABLE 1

| Components (wt %) | Example 1 | Example 2 | Example 3 |
| --- | --- | --- | --- |
| 4,5-Dichloro-2-n-Octyl-4-isothiazolin-3-one | 3 | 3 | 3 |
| 2-N-Octyl-4-isothiazolin-3-on | 7 | 5 | 5 |
| Thiabendazole | — | 2 | — |
| Zinc pyrithione | — | — | 2 |
| Simethicone | 9 | 9 | 9 |
| Octamethylcyclotetrasiloxane | 6 | 6 | 6 |
| Binder (Polyalkyl acrylate) | 40 | 40 | 40 |
| Purified water | To 100 | To 100 | To 100 |

2. Preparation of Dilutions of Antimicrobial Compositions 100 parts by weight of each of the prepared antimicrobial compositions was diluted in 900 parts by weight of water. At this time, 0.1 parts by weight of organosiloxane was used as an antifoaming agent.

3. Preparation of Filtration Media

The backing media of a filtration media was treated with each of the diluted antimicrobial compositions according to the method shown in FIG. 2, and was used to prepare a filtration media having a cover web, a filtering part and a backing media.

Specifically, the backing media was dipped in each of the dilutions 11 prepared in Examples, and then squeezed 12 was dried 14 while it was wound 16. The wound backing media 16 was unwound while it was laminated with a filtering part and then a cover web, thus preparing a filtration media.

The backing media consisted of a net made of polypropylene, the cover web consisted of polyester spunbonded nonwoven fabric having a basis weight of 15 g, and the filtering part consisted of electrostatic nonwoven fabric made of polypropylene, which has a basis weight of 50 g.

COMPARATIVE EXAMPLE 1

A filtration media was prepared in the same manner as in Example 1 using the same backing media, filtering part and cover web as in Example 1, except that treatment with the antimicrobial composition was not conducted.

TEST EXAMPLE 1

An antibacterial test was conducted in the following manner in accordance with the method provided in KS K 0693-2001.

1. Bacterial Strains used

*Escherichia coli* ATCC 25922
*Staphylococcus aureus* ATCC 6538
*Klebsiella pneumoniae* ATCC 4352
*Bacillus subtilis* ATCC 6633

2. Medium and Reagents (1) Nutrient Medium 5 g of peptone (BACTO-Peptone Ehsms Thiotone) and 3 g of beef extract were dissolved in 1,000 ml of distilled water and then adjusted to pH 6.8±0.2 (25° C.) with 0.1M NaOH. Then, the solution was sterilized in a high-pressure sterilizer at a vapor pressure of 1,055 $g/cm^2$ and a temperature of 120±2° C. for 20 minutes. When a nutrient agar medium was prepared, 15 g of agar was added before the sterilization.

(2) Physiological Salt Solution 5 g of NaCl was dissolved in 1,000 ml of distilled water, and then sterilized in a high-pressure sterilizer at a vapor pressure of 1,055 $g/cm^2$ and a temperature of 120±2° C. for 20 minutes.

(3) Neutralizing Solution 5 g of NaCl and 2 g of a non-ionic surfactant (Tween 80) were dissolved in 1,000 ml of distilled water, and then sterilized in a high-pressure sterilizer at a vapor pressure of 1,055 $g/cm^2$ and a temperature of 12±2° C. for 20 minutes.

3. Test Method (KS K0693-2001 Method)

(1) Preparation of Inocula

For the preparation of inocula, each of said bacterial strains was inoculated into a 100-ml erlenmeyer flask containing 20 ml of the nutrient medium, and was shake-cultured at 37±1° C. for 18-24 hours. The O.D. (optical density) at 660 nm of the cultured medium was measured with a spectrophotometer to count the number of viable bacteria. 0.2 ml of a bacterial medium (nutrient medium), prepared by 20-fold diluting the cultured medium to have an initial bacterial count of $2.1 \times 10^4$/ml, $2.2 \times 10^4$/ml or $2.4 \times 10^4$/ml as shown in Table 1, was used as inoculum.

(2) Preparation of Test Groups and Control Group 0.4 g of each of test samples was prepared using each of the filters prepared in Examples 1-3, and 0.4 g of a control group was prepared using a filter (Comparative Example 1), which had the same material and structure of the test samples, but was not treated with the antimicrobial composition.

For each of the bacterial strains and each of Examples, 6 control samples and 3 test samples were prepared, and each of the samples was placed into an about 30-ml glass container equipped with a screw cover. The test sample and control sample placed into one container could absorb the inocula, and care was taken such that there was no liquid flowing in the glass container. Among the six control samples, three control samples were used for the measurement of viable bacterial number just after inoculation, and the remaining three control samples were used for the measurement of viable bacterial number after culture.

(3) Environmental Conditions for Treatment 5 cycles each consisting of 12 hours of 30° C. temperature/90% relative humidity (RH) and 12 hours of 60° C. temperature/90% relative humidity (RH) were conducted.

(4) Inoculation and Culture of Test Samples and Control Samples 0.2 ml of the inoculum was taken, and carefully inoculated uniformly onto the test sample and control sample contained in each of the glass containers. After the inoculation, the container was closed with the cover. The glass container containing each of the three control samples and three test samples, inoculated with the test bacterial medium, was incubated at 37±1° C. for 18 hours.

(5) Extraction of Bacterial Medium and Measurement of Initial Cell Number After Inoculation 20 ml of the neutralization solution maintained at 0° C. was placed into the container containing each of the inoculated control samples as soon as possible after the inoculation and was severely shaken, and a bacterial medium was extracted from each of the samples and then serially diluted with physiological salt solution. 1.0 ml of each of the dilutions was taken, and placed onto a Petri dish. Then, about 15 ml of a nutrient agar medium maintained at 45° C. was poured into the Petri dish and uniformly mixed with the dilution, and the mixture was solidified at room temperature.

(6) Extraction and Evaluation of Bacterial Medium After 18 Hours of Culture

After 18 hours of the culture, 20 ml of the neutralization solution maintained at 0° C. was placed into the glass container containing each of the control samples and the test samples, and the container was severely shaken. Then, a bacterial medium was extracted from each of the samples and serially diluted with physiological salt solution. 1.0 ml of each of the dilutions was placed into a Petri dish. Then, about 15 ml of a nutrient agar medium maintained at 45° C. was poured into the Petri dish and uniformly mixed with the dilution, and the mixture was solidified at room temperature.

The number of viable bacteria in the extracted bacterial medium was counted, and bacterial reduction rate was calculated according to Equation 1 below.

$$\text{Reduction rate}(\%) = [(Mb-Mc)/Mb] \times 100 \quad \text{[Equation 1]}$$

wherein Mb represents the number of viable bacteria in the control sample after 18-hr culture, and Mc represents the number of viable bacteria in the test sample after 18-hr culture.

The measurement results are shown in Table 2 below.

TABLE 2

| Bacterial strains used | | Control group (Comparative Example 1) | Examples 1-3 |
|---|---|---|---|
| Escherichia coli ATCC 25922 | Initial bacterial number | $2.1 \times 10^4$ | $2.1 \times 10^4$ |
| | After 18 hours | $4.0 \times 10^7$ | <10 |
| | Bacterial reduction rate (%) | | 99.9 |
| Staphylococcus aureus ATCC 6538 | Initial bacterial number | $2.4 \times 10^4$ | $2.4 \times 10^4$ |
| | After 18 hours | $4.5 \times 10^6$ | <10 |
| | Bacterial reduction rate (%) | | 99.9 |
| Klebsiella pneumoniae ATCC 4532 | Initial bacterial number | $2.1 \times 10^4$ | $2.1 \times 10^4$ |
| | After 18 hours | $7.8 \times 10^6$ | <10 |
| | Bacterial reduction rate (%) | | 99.9 |
| Pseudomonas aeruginosa ATCC 27853 | Initial bacterial number | $2.2 \times 10^4$ | $2.2 \times 10^4$ |
| | After 18 hours | $1.2 \times 10^7$ | <10 |
| | Bacterial reduction rate (%) | | 99.9 |

As can be seen from the test results in Table 2 above, Examples 1, 2 and 3 all showed a bacterial reduction rate higher than 99.9%. The bacterial reduction rate higher than 99.9% suggests that the bacteria were all killed.

TEST EXAMPLE 2

Antifungal Test (Fungus Resistance Test)

An antifungal test was conducted in the following manner in accordance with the ISO 846 B method.

As test devices, Clean Bench (Su Gong Yang Heng Co., Korea) and a constant temperature/humidity chamber (Sanyo) were used, and as test fungal strains, a mixture of the following fungal strains was used:

Aspergillus niger ATCC 9642
Penicillium pinophilum ATCC 111797
Chaetomium globosum ATCC 6205
Gliocladium virens ATCC 9645
Aurebasidium pullulans ATCC 15233.

As a nutrient medium, a medium having the composition shown in Table 3 below was used.

TABLE 3

| $NaNO_3$ | 2.0 g |
|---|---|
| $KH_2PO_4$ | 0.7 g |
| $K_2HPO_4$ | 0.3 g |
| KCl | 0.5 g |
| $MgSO_4 \cdot 7H_2O$ | 0.5 g |
| $FeSO_4 \cdot 7H_2O$ | 0.01 g |
| Agar | 20 g |
| Glucose | 30 g |
| Deionized water | 1 L |

Using a mixed spore suspension of said five fungal strains, the fungal growth inhibitory capabilities of the filters prepared in Examples 1-3 and Comparative Example 1 above were analyzed.

Specifically, each of the filters prepared in Examples 1-3 and Comparative Example 1 was placed on a culture dish containing the nutrient medium prepared as described above, and the mixed spore suspension was sprayed uniformly onto the samples and the medium. Then, the samples and the medium were placed in an incubator at a temperature of 25-28° C. and a relative humidity of more than 85%, while the growth rate of the fungi was measured. The measurement results are shown in Table 4 below.

TABLE 4

| | Evaluation | | | |
|---|---|---|---|---|
| Samples | After 1 week | After 2 weeks | After 3 weeks | After 4 weeks |
| Comparative Example 1 | 1 | 3 | 4 | 4 |
| Example 1 | 0 | 0 | 1 | 1 |
| Example 2 | 0 | 0 | 0 | 0 |
| Example 3 | 0 | 0 | 0 | 1 |

<Evaluation of Results>

0: the growth of the fungi in the samples was not observable.
1: the growth of the fungi in samples was about 10%.
2: the growth of the fungi in samples was 10-30%.
3: the growth of the fungi in samples was 30-60%.
4: the growth of the fungi in samples was more than 60%.

Figure 4A:
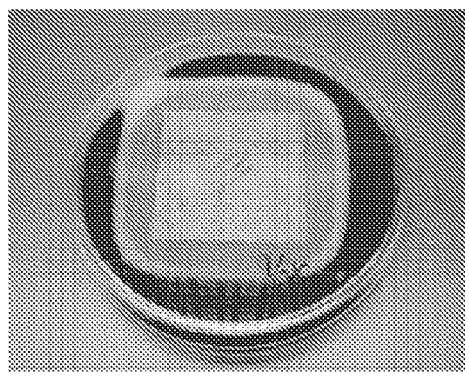
FIG. 4a is a photograph showing the results of a test conducted in accordance with the ISO 846 B test method to examine the fungal resistance of the inventive filtration media.
Figure 4B:
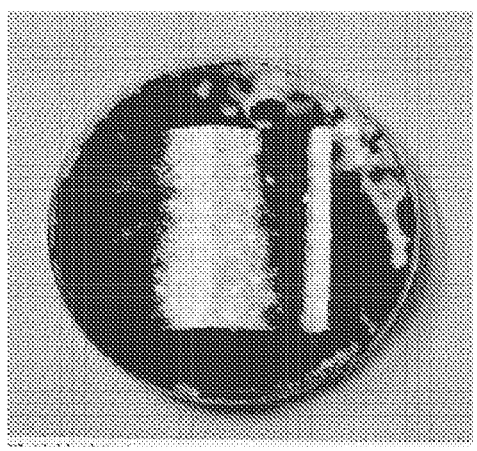
FIG. 4b is a photograph showing the results of a test conducted in accordance with the ISO 846 B test method to examine the fungal resistance of a cabin air filter, which is one example of a prior filtration media.
Figure 4C:
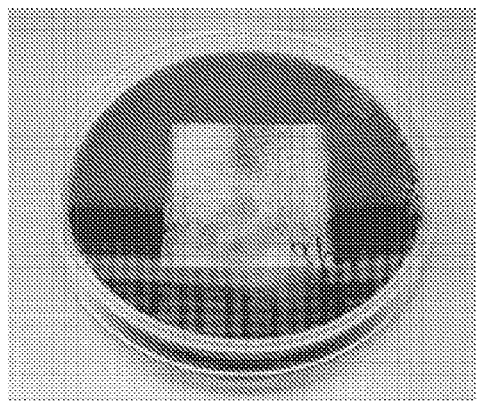
FIG. 4c is a photograph showing the results of a test conducted in accordance with the ISO 846 B test method to examine the fungal resistance of a room air purifier filter media, which is one example of prior filtration media.

FIG. 4a shows the results of the test conducted using Example 1, and FIG. 4b shows the results of the test conducted using Comparative Example 1. For reference, FIG. 4c is a photograph showing the fungal resistance of a room air purifier filter media, which is one example of prior filtration media.

As can be seen from the above test results, the antimicrobial composition according to the present invention had excellent antibacterial and antifungal properties, and the filter prepared using the inventive antimicrobial composition also had very excellent antibacterial and antifungal properties.

INDUSTRIAL APPLICABILITY

As can be seen from the foregoing, according to the present invention provides, the filter media is prepared using the antimicrobial composition having antibacterial and antifungal properties, and the filter is prepared using the filtration media. Thus, the filter according to the present invention has excellent antibacterial and antifungal properties, can filter microorganisms in air, including bacteria and fungi, and can prevent the filtered microorganisms from growing in the filtration media.

Although the preferred embodiment of the present invention has been described for illustrative purposes, those skilled in the art will appreciate that various modifications, additions and substitutions are possible, without departing from the scope and spirit of the invention as disclosed in the accompanying claims.

The invention claimed is:

1. An antimicrobial composition comprising:
    4,5-dichloro-2-n-octyl-4-isothiazolin-3-one;
    2-N-octyl-4-isothiazolin-3-one;
    at least one stabilizer selected from the group consisting of volatile silicone oil and silicone resin;
    at least one binder selected from the group consisting of acryl resin, urethane resin and silicone resin; and
    water.

2. The antimicrobial composition according to claim 1, further comprising at least one selected from the group consisting of thiabendazole, nano-silver and zinc pyrithione.

3. The antimicrobial composition according to claim 1, which comprises 1 to 5 wt % of the 4,5-dichloro-2-n-octyl- 4-isothiazolin-3-one, 1 to 15 wt % of the 2-N-octyl-4-isothiazolin-3-one, 1 to 10 w % of the stabilizer, 20 to 80 wt % of the binder, and a residual amount of water, based on the total weight of the composition.

4. The antimicrobial composition according to claim 1, which is in the form of a water-dispersible composition.

5. The antimicrobial composition according to claim 1, which further comprises an anti-foaming agent.

6. The antimicrobial composition according to claim 5, wherein the anti-foaming agent is selected from the group consisting of organo-siloxane and polyalkylene glycol derivatives.

7. The antimicrobial composition according to claim 5, wherein the anti-foaming agent is contained in an amount of 0.01 to 0.5 wt % based on the total weight of the composition.

8. A method for preparing a filtration media having a cover web, a filtering part and a backing media, the method comprising the steps of:
   diluting the antimicrobial composition according to claim 1 with water to prepare a dilution of the antimicrobial composition;
   treating the cover web or backing media of the filtration media with the dilution and drying the cover web or the backing media; and
   arranging the cover web or the backing together with other members of the filtration media.

9. The method according to claim 8, wherein the dilution is prepared by diluting 100 parts by weight of the antimicrobial composition with 500 to 5000 parts by weight of water.

10. The method according to claim 8, wherein the step of treating the cover web or backing media of the filtration media with the dilution is conducted by dipping the cover web or the backing media in the dilution or by spraying the dilution onto the cover web or the backing media.

11. A filtration media prepared according to the method according to claim 8.

12. An air filter comprising:
   a filtration media according to claim 11; and
   a filter frame for settling the filtration media.

* * * * *

UNITED STATES PATENT AND TRADEMARK OFFICE
CERTIFICATE OF CORRECTION

PATENT NO.       : 7,942,957 B2
APPLICATION NO.  : 12/097060
DATED            : May 17, 2011
INVENTOR(S)      : Lee et al.

It is certified that error appears in the above-identified patent and that said Letters Patent is hereby corrected as shown below:

First page, left column, line 2 under Inventors, delete "Kyungki-di (KR)" and insert --Kyungki-do (KR)--.

Col. 2, line 39, delete "Stilt" and insert --Still--.

Col. 6, line 56, delete "on" and insert --one--.

Col. 9, line 42, delete "111797" and insert --11797--.

Col. 9, line 45, delete "Aurebasidium" and insert --Aureobasidium--.

Col. 11, line 2, delete "10 w %" and insert --10 wt %--.

Signed and Sealed this
Twelfth Day of July, 2011

David J. Kappos
*Director of the United States Patent and Trademark Office*